(12) United States Patent
Yoshida et al.

(10) Patent No.: US 8,962,287 B2
(45) Date of Patent: Feb. 24, 2015

(54) SCYLLO-INOSITOL-PRODUCING CELL AND SCYLLO-INOSITOL PRODUCTION METHOD USING SAID CELLS

(75) Inventors: Kenichi Yoshida, Hyogo (JP); Hitoshi Ashida, Hyogo (JP)

(73) Assignee: National University Corporation KOBE University, Kobe-Shi, Hyogo (JP)

( * ) Notice: Subject to any disclaimer, the term of this patent is extended or adjusted under 35 U.S.C. 154(b) by 441 days.

(21) Appl. No.: 13/127,047

(22) PCT Filed: Oct. 30, 2009

(86) PCT No.: PCT/JP2009/005782
§ 371 (c)(1),
(2), (4) Date: Apr. 30, 2011

(87) PCT Pub. No.: WO2010/050231
PCT Pub. Date: May 6, 2010

(65) Prior Publication Data
US 2011/0207188 A1    Aug. 25, 2011

(30) Foreign Application Priority Data
Oct. 31, 2008    (JP) ................................. 2008-281348

(51) Int. Cl.
*C12P 7/02*    (2006.01)
*C12P 7/18*    (2006.01)
*C12N 9/04*    (2006.01)
*C12N 9/02*    (2006.01)

(52) U.S. Cl.
CPC ... *C12P 7/18* (2013.01); *C12P 7/02* (2013.01); *C12N 9/0006* (2013.01); *C12N 9/0008* (2013.01)
USPC .......................................... 435/155; 435/189

(58) Field of Classification Search
CPC ...................................................... C12P 7/02
See application file for complete search history.

(56) References Cited

U.S. PATENT DOCUMENTS

2006/0240534 A1    10/2006    Yamaguchi et al.
2008/0050774 A1    2/2008    Berka et al.

FOREIGN PATENT DOCUMENTS

WO    WO2005/035774 A1    4/2005

OTHER PUBLICATIONS

Masson et al.: "Strain: BFS3018", INRA, Oct. 8, 1997, XP002677029, Retrieved from the Internet: URL:http://locus.jouy.inra.fr/cgi-bin/dev/chiapell/result-old.oper1?STRAIN=BFS3018 &NAME= (retrieved on Jun. 1, 2012).
Morinaga Tetsuro et al.: "Identification of two scyllo-inositol dehydrogenases in *Bacillus subtilis*", May 2010, Microbiology (Reading, England) May 2010 LNKD-PUBMED:20133360, vol. 156, NR.PT 5, pp. 1538-1546.
Yoshida et al., "Genetic Modification of *Bacillus subtilis* for Production of D-chiro-Inositol, an Investigational Drug Candidate for Treatment of Type 2 Diabetes and Polycystic Ovary Syndrome", Appl. Environ Microbiol., 2006, v72, pp. 1310-1315.
Database UniProtKB, accession P40332, annotation updated: Jun. 10, 2008, [retrieved on Jan. 15, 2010], Roche B et al., <http://www.ncbi.nlm.nih.gov/sviewer/viewer.fcgi?2851424:PROT:6711647>, Definition Putative oxidoreductase yisS.
Hipps et al., "Interconversion of Myo- and Scyllo-Inositol with Simultaneous Formation of Neo-Inositol by an NADP+ Dependent Epimerase From Bovine Brain", Biochemical and Biophysical Research Communications, 1977, vol. 77, No. 1, pp. 340-346.

*Primary Examiner* — Rebecca Prouty
(74) *Attorney, Agent, or Firm* — Don D. Cha; Hamilton DeSanctis & Cha, LLP (57)    ABSTRACT

An object of the present invention is to provide a cell capable of efficiently producing scyllo-inositol from myo-inositol and a simple method of manufacturing scyllo-inositol using the cell. The above-mentioned object is achieved by a *Bacillus subtilis* cell, in which a function of a protein having a scyllo-inositol dehydrogenase activity is lost, and the manufacture of scyllo-inositol using the cell, based on a novel finding that the protein having a scyllo-inositol dehydrogenase activity and a protein having a 2-keto-myo-inositol ketoreductase function are present in *Bacillus subtilis*.

9 Claims, 6 Drawing Sheets

FIGURE 1

| GENE | RATIO OF EXPRESSION AMOUNTS<br>WILD-TYPE WITH SI/MI<br>(STRAIN YF256 WITH MI/WITHOUT MI) | SIGNAL INTENSITY<br>WILD-TYPE WITH SI<br>(STRAIN YF256 WITH MI) |
|---|---|---|
| iolG | 0.43 (0.62) | 49664 (407030) |
| yfiI | 1.5 (0.77) | 6773 (8461) |
| yhjJ | 1.4 (13.4) | 20019 (7565) |
| yisS | 2.8 (1.9) | 78748 (121930) |
| yrbE | 2.2 (0.91) | 8011 (21540) |
| yteU | 1.6 (1.8) | 4304 (4687) |
| yulF | 1.8 (26.3) | 2566 (4794) |
| yvaA | 1.4 (0.83) | 84956 (11108) |

SCYLLO-INOSITOL-PRODUCING CELL AND SCYLLO-INOSITOL PRODUCTION METHOD USING SAID CELLS

CROSS-REFERENCE TO RELATED APPLICATIONS

The present application is U.S. National Phase Entry of PCT/JP2009/005782, filed Oct. 30, 2009, which claims priority from Japanese Patent Application No. 2008-281348, all of which are hereby incorporated by reference in their entirety.

FIELD OF THE INVENTION

The present invention relates to a scyllo-inositol (SI)-producing cell and a method of manufacturing scyllo-inositol using the cell. More specifically, a function of a protein having a scyllo-inositol dehydrogenase activity is lost or reduced in the cell.

BACKGROUND OF THE INVENTION

Scyllo-Inositol is one of the stereoisomers of myo-inositol (MI) and is a compound widely found in animals and plants. scyllo-Inositol is expected for applications such as a therapeutic drug for Alzheimer's disease, a raw material for the synthesis of bioactive substances, and a raw material for the synthesis of liquid crystal compounds. While myo-inositol is supplied at low cost, scyllo-inositol is an expensive compound. Hence, a variety of studies have been carried out on a method of manufacturing scyllo-inositol involving the use of myo-inositol as a raw material.

Examples of the method of manufacturing scyllo-inositol by use of a chemical synthesis technique include a method involving providing scyllo-inositol by oxidizing myo-inositol with a platinum catalyst to afford 2-keto-myo-inositol (scyllo-inosose) and subsequently subjecting the resultant to esterification followed by reduction and hydrolysis.

Further, there is disclosed, as a method of converting myo-inositol to scyllo-inositol, a method involving the use of a bacterium belonging to the genus *Pseudomonas* and a bacterium belonging to the genus *Acetobacter* separated from the nature. The method involves providing scyllo-inositol by producing 2-keto-myo-inositol from myo-inositol using the above-mentioned bacterium and subjecting 2-keto-myo-inositol to chemical reduction (Patent Literature 1).

Strains capable of producing a small amount of scyllo-inositol from myo-inositol were obtained from bacteria belonging to the genus *Acetobacter* and the like (Patent Literature 2). It is known that an enzyme for stereospecifically reducing 2-keto-myo-inositol to scyllo-inositol in an NADPH-dependent manner is functioning in those strains.

There is a report that a strain capable of efficiently producing D-chiro-inositol from myo-inositol was obtained by the genetic modification of genes involved in inositol catabolism in a bacterium belonging to the genus *Bacillus* (Patent Literature 3 and Non Patent Literature 1). Such strain (strain YF256) lacks the iolE gene and the iolR gene involved in inositol catabolism.

[PTL 1] JP 3981597 B2
[PTL 2] WO 2005/035774 A1
[PTL 3] JP 2006-141216 A
[NPL 1] Appl Environ Microbiol. 2006 Feb.; 72(2): 1310-5.

SUMMARY OF THE INVENTION

Technical Problem

An object of the present invention is to provide a cell capable of efficiently producing scyllo-inositol from myo-inositol and a simple method of manufacturing scyllo-inositol using the cell.

Solution to Problem

In order to solve the above-mentioned problem, the inventors of the present invention have made extensive studies. As a result, the inventors have newly confirmed that a protein having a scyllo-inositol dehydrogenase activity and a protein having a 2-keto-myo-inositol ketoreductase activity are present in *Bacillus subtilis*, and have found that scyllo-inositol can be efficiently produced by a scyllo-inositol-producing cell, in which a function of a protein having a scyllo-inositol dehydrogenase activity is lost. Thus, the present invention has been completed.

That is, the present invention includes the following.

1. A scyllo-inositol-producing cell, in which at least a function of a protein having a scyllo-inositol dehydrogenase activity is lost or reduced.

2. A scyllo-inositol-producing cell according to the item 1, furthermore, in which a function of a protein having a 2-keto-myo-inositol dehydratase activity and a function of a repressor protein for genes involved in inositol catabolism are lost or reduced.

3. A scyllo-inositol-producing cell according to the item 1 or 2, in which the function of the protein having a scyllo-inositol dehydrogenase activity is lost or reduced by the artificial disruption of a gene encoding the protein having a scyllo-inositol dehydrogenase activity.

4. A scyllo-inositol-producing cell according to any one of the items 1 to 3, in which the scyllo-inositol dehydrogenase activity is an activity of dehydrogenating a hydroxy group at the 2-position of scyllo-inositol.

5. A scyllo-inositol-producing cell according to any one of the items 1 to 4, in which the protein having a scyllo-inositol dehydrogenase activity is a protein encoded by any one selected from the following DNAs (a) to (c):
 (a) a DNA including a base sequence set forth in SEQ ID NO: 1;
 (b) a DNA including a base sequence having substitutions, deletions, insertions, and/or additions of one or more nucleotides in the base sequence set forth in SEQ ID NO: 1, and encoding the protein having a scyllo-inositol dehydrogenase activity; and
 (c) a DNA being hybridized with the DNA including the base sequence set forth in SEQ ID NO: 1 under a stringent condition, and encoding the protein having a scyllo-inositol dehydrogenase activity.

6. A scyllo-inositol-producing cell according to any one of the items 1 to 5, in which the protein having a scyllo-inositol dehydrogenase activity is any one selected from the following proteins (a) to (c):
 (a) a protein including an amino acid sequence set forth in SEQ ID NO: 2;
 (b) a protein including an amino acid sequence having deletions, substitutions, insertions, and/or additions of one or more amino acids in the amino acid sequence set forth in SEQ ID NO: 2, and having a scyllo-inositol dehydrogenase activity; and (c) a protein including an amino acid sequence having 40% or more homology to the amino acid sequence set forth in SEQ ID NO: 2, and having a scyllo-inositol dehydrogenase activity.

7. A scyllo-inositol-producing cell according to any one of the items 1 to 6, in which the protein having a scyllo-inositol dehydrogenase activity functions in an NAD$^+$-dependent manner.

8. A scyllo-inositol-producing cell according to any one of the items 1 to 7, in which a protein having a 2-keto-myo-inositol ketoreductase activity is functioning.

9. A scyllo-inositol-producing cell according to the item 8, in which the protein having a 2-keto-myo-inositol ketoreductase activity is a protein encoded by any one selected from the following DNAs (a) to (c):
(a) a DNA including a base sequence set forth in SEQ ID NO: 3;
(b) a DNA including a base sequence having substitutions, deletions, insertions, and/or additions of one or more nucleotides in the base sequence set forth in SEQ ID NO: 3, and encoding the protein having a 2-keto-myo-inositol ketoreductase activity; and
(c) a DNA being hybridized with the DNA including the base sequence set forth in SEQ ID NO: 3 under a stringent condition, and encoding the protein having a 2-keto-myo-inositol ketoreductase activity.

10. A scyllo-inositol-producing cell according to the item 8, in which the protein having a 2-keto-myo-inositol ketoreductase activity is any one selected from the following proteins (a) to (c):
(a) a protein including an amino acid sequence set forth in SEQ ID NO: 4;
(b) a protein including an amino acid sequence having deletions, substitutions, insertions, and/or additions of one or more amino acids in the amino acid sequence set forth in SEQ ID NO: 4, and having a 2-keto-myo-inositol ketoreductase activity; and
(c) a protein including an amino acid sequence having 40% or more homology to the amino acid sequence set forth in SEQ ID NO: 4, and having a 2-keto-myo-inositol ketoreductase activity.

11. A scyllo-inositol-producing cell according to any one of the items 1 to 10, in which the cell is a bacterium belonging to the genus *Bacillus*.

12. A scyllo-inositol-producing cell according to any one of the items 1 to 11, in which the cell is a *Bacillus subtilis* strain TM030 having an accession number of FERM ABP-11185 (domestic deposit number: FERM P-21700, domestic deposit date: Oct. 8, 2008).

13. A scyllo-inositol-producing cell according to any one of the items 1 to 12, furthermore, in which a function of a protein having a scyllo-inosose isomerase activity is reduced or lost.

14. A method of manufacturing scyllo-inositol, including the step of culturing the cell according to any one of the items 1 to 13 in the presence of myo-inositol.

15. A method of manufacturing scyllo-inositol according to the item 14, further including the steps of: removing the cell from a filtrate of the culture obtained in the culturing step; and isolating scyllo-inositol from the filtrate after the removing of the cell.

Advantageous Effects of Invention

The cell of the present invention can efficiently produce scyllo-inositol, which may be used for a therapeutic drug for Alzheimer's disease and the like, using myo-inositol, which is inexpensive, as a raw material intracellularly. Further, the method of manufacturing scyllo-inositol of the present invention using such cell allows scyllo-inositol to be produced simply in one step without the use of an additive such as a reducing agent.

DETAILED DESCRIPTION OF THE INVENTION

The present invention relates to a cell capable of efficiently producing scyllo-inositol because a function of a protein having a scyllo-inositol dehydrogenase activity, which is present in a original cell, is lost or reduced in the cell.

The cell in which (wherein) a function of a protein is lost or reduced used herein is exemplified by a cell in which a function of a protein of interest itself is reduced or absent, an amount of the protein is reduced, or an expression of the protein is reduced as compared to a wild-type cell. Specifically, the cell in which (wherein) a function of a protein is lost or reduced is exemplified by a cell in which a mutation has been introduced into a gene encoding a protein of interest or a cell in which the gene has been disrupted. The cell of the present invention may be a naturally occurring cell, or may be a cell produced by the artificial disruption of the gene. The cell of the present invention is preferably a cell produced by the artificial disruption of a gene encoding a protein of interest.

The "cell" used herein may be any cell as long as an enzyme involved in inositol catabolism is included and a function of a protein having a scyllo-inositol dehydrogenase activity is lost or reduced in the cell. The kind of the cell is not limited and a microorganism, an animal cell, a plant cell, or the like may be used. A microorganism including a group of enzymes involved in inositol catabolism (having genes or (a) operon(s) involved in inositol catabolism) may be preferably used. The microorganism is preferably a bacterium. Bacteria known to form genes involved in inositol catabolism are exemplified by bacteria belonging to the genera *Bacillus, Geobacillus, Ralstonia*, and *Salmonella*. Further, bacteria belonging to the genera *Cryptococcus, Enterobacter, Rhizobium*, and *Shinorhizobium* may also have genes involved in inositol catabolism and those bacteria may also be used. In particular, it is preferred to use a bacterium belonging to the genus *Bacillus* and it is more preferred to use *Bacillus subtilis*.

The enzyme involved in inositol catabolism is exemplified by at least scyllo-inositol dehydrogenase, 2-keto-myo-inositol ketoreductase, and myo-inositol-2-dehydrogenase. The enzyme is further exemplified by scyllo-inosose isomerase, 2-keto-myo-inositol dehydratase, and the like. The enzyme involved in inositol catabolism includes enzymes encoded by genes involved in inositol catabolism. For example, in *Bacillus subtilis*, myo-inositol-2-dehydrogenase, scyllo-inosose isomerase, 2-keto-myo-inositol dehydratase, and the like are encoded by genes involved in inositol catabolism.

At least, a function of a protein having a scyllo-inositol dehydrogenase activity is lost or reduced in the cell of the present invention. scyllo-Inositol dehydrogenase catalyzes a reaction of converting scyllo-inositol to 2-keto-myo-inositol and has an activity of dehydrogenating a hydroxy group at the 2-position of scyllo-inositol. Further, the scyllo-inositol dehydrogenase activity is dependent on $NAD^{\pm}$.

The protein having a scyllo-inositol dehydrogenase activity preferably includes a protein encoded by any one selected from the following DNAs (a) to (c): (a) a DNA including a base sequence set forth in SEQ ID NO: 1; (b) a DNA including a base sequence having substitutions, deletions, insertions, and/or additions of one or more nucleotides in the base sequence set forth in SEQ ID NO: 1, and encoding the protein having a scyllo-inositol dehydrogenase activity; and (c) a DNA being hybridized with the DNA including the base sequence set forth in SEQ ID NO: 1 under a stringent condition, and encoding the protein having a scyllo-inositol dehydrogenase activity. Alternatively, the protein having a scyllo-inositol dehydrogenase activity includes any one selected from the following proteins (a) to (c): (a) a protein including an amino acid sequence set forth in SEQ ID NO: 2; (b) a protein including an amino acid sequence having deletions, substitutions, insertions, and/or additions of one or more amino acids in the amino acid sequence set forth in SEQ ID NO: 2, and having a scyllo-inositol dehydrogenase activity; and (c) a protein including an amino acid sequence having 40% or more homology to the amino acid sequence set forth in SEQ ID NO: 2, and having a scyllo-inositol dehydrogenase activity.

Further, the cell of the present invention preferably includes a protein having a 2-keto-myo-inositol ketoreductase activity, a function of the protein being maintained. 2-Keto-myo-inositol ketoreductase catalyzes a reaction of converting 2-keto-myo-inositol to scyllo-inositol. Further, the 2-keto-myo-inositol ketoreductase activity is dependent on NADPH.

The protein having a 2-keto-myo-inositol ketoreductase activity preferably includes a protein encoded by any one selected from the following DNAs (a) to (c): (a) a DNA including a base sequence set forth in SEQ ID NO: 3; (b) a DNA including a base sequence having substitutions, deletions, insertions, and/or additions of one or more nucleotides in the base sequence set forth in SEQ ID NO: 3, and encoding the protein having a 2-keto-myo-inositol ketoreductase activity; and (c) a DNA being hybridized with the DNA including the base sequence set forth in SEQ ID NO: 3 under a stringent condition, and encoding the protein having a 2-keto-myo-inositol ketoreductase activity. Alternatively, the protein having a 2-keto-myo-inositol ketoreductase activity includes any one selected from the following proteins (a) to (c): (a) a protein including an amino acid sequence set forth in SEQ ID NO: 4; (b) a protein including an amino acid sequence having deletions, substitutions, insertions, and/or additions of one or more amino acids in the amino acid sequence set forth in SEQ ID NO: 4, and having a 2-keto-myo-inositol ketoreductase activity; and (c) a protein including an amino acid sequence having 40% or more homology to the amino acid sequence set forth in SEQ ID NO: 4, and having a 2-keto-myo-inositol ketoreductase activity.

The DNA to be hybridized under a stringent condition used herein means, for example, a DNA obtained by employing a colony hybridization method, a plaque hybridization method, a Southern blot hybridization method, or the like using as a probe a DNA having the base sequence set forth in SEQ ID NO: 1 or 3 or a part thereof, i.e., a DNA fragment. A specific example thereof may be a DNA which may be identified by carrying out hybridization at 65° C. in the presence of 0.7 to 1.0 M sodium chloride using a filter having immobilized thereon a colony- or plaque-derived DNA and then washing the filter under a condition of 65° C. using an SSC solution having a 0.1- to 2-fold concentration (SSC solution having a 1-fold concentration has the following composition: 150 mM sodium chloride and 15 mM sodium citrate). The hybridization may be carried out in accordance with the methods described, for example, in Molecular Cloning, A Laboratory Manual, Second Edition, Cold Spring Harbor Laboratory Press, 1989 (hereinafter, abbreviated as Molecular Cloning, Second Edition), Current Protocols in Molecular Biology, John Wiley & Sons, 1987-1997 (hereinafter, abbreviated as Current Protocols in Molecular Biology), and DNA Cloning 1: Core Techniques, A Practical Approach, Second Edition, Oxford University (1995). Specific examples of the DNA which may be hybridized may include a DNA including a base sequence having at least 30% or more homology to the base sequence set forth in SEQ ID NO: 1 or 3, a DNA including a base sequence having preferably 60% or more, more preferably 80% or more, even more preferably 90% or more, most preferably 98% or more homology.

In the present invention, the protein encoded by a base sequence having substitutions, deletions, insertions, and/or additions of one or more nucleotides in the base sequence set forth in SEQ ID NO: 1 or 3 and the protein including an amino acid sequence having deletions, substitutions, insertions, and/or additions of one or more amino acids in the amino acid sequence set forth in SEQ ID NO: 2 or 4 may be obtained using the site-directed mutagenesis method described, for example, in Molecular Cloning, Second Edition, Current Protocols in Molecular Biology, Nucleic Acids Research, 10, 6487 (1982), Proc. Natl. Acad. Sci., USA, 79, 6409 (1982), Gene, 34, 315 (1985), Nucleic Acids Research, 13, 4431 (1985), and Proc. Natl. Acad. Sci USA, 82, 488 (1985). The number of the nucleotides or amino acids to be deleted, substituted, inserted, and/or added is 1 or more. The number is not particularly limited but is such a number that may be deleted, substituted, or added by a known art such as the above-mentioned site-directed mutagenesis method. The number is, for example, 1 to several tens, preferably 1 to 20, more preferably 1 to 10, even more preferably 1 to 5.

Further, in the present invention, proteins having functions of scyllo-inositol dehydrogenase activity and myo-inositol-2-dehydrogenase activity have at least 40% or more, preferably 80% or more, more preferably 90% or more, particularly preferably 95% or more homology to the amino acid sequences set forth in SEQ ID NO: 2 and 4, respectively, the homology being calculated using analysis software such as a BLAST [J. Mol. Biol., 215, 403 (1990)] or a FASTA [Methods in Enzymology, 183, 63 (1990)]. Such protein including an amino acid sequence having 40% or more homology to the amino acid sequence set forth in SEQ ID NO: 2 or 4 includes a protein having a stereostructure similar to a protein including the amino acid sequence set forth in SEQ ID NO: 2 or 4.

Whether or not a protein of interest has a scyllo-inositol dehydrogenase activity or a myo-inositol-2-dehydrogenase activity and whether or not a gene of interest encodes a protein having such activity may be confirmed by a method such as an enzymological assay known per se. In addition, this may also be confirmed, for example, by growing a strain obtained by allowing a function of a protein of interest to be lost artificially in a medium containing only scyllo-inositol or only 2-keto-myo-inositol as a carbon source.

It is preferred that a function of a protein having a 2-keto-myo-inositol dehydratase activity and a function of a repressor protein for genes involved in inositol catabolism are lost or reduced in the cell of the present invention.

It is more preferred that a function of a protein having a scyllo-inosose isomerase activity is lost or reduced in the cell of the present invention.

In the production of the cell of the present invention, a method involving allowing a function of a protein of interest to be lost or reduced artificially is exemplified by a method involving disrupting a gene encoding the protein of interest and a general method involving the use of a mutation may be employed. For example, as physical and/or chemical mutagenic treatments, there are given, not only a physical mutation method such as UV irradiation or radiation irradiation but also a chemical mutation method by mixing of a mutation agent such as N-nitrosoguanidine, ethyl methanesulfonate, nitrous acid, methyl methanesulfonate, an acridine pigment, benzopyrene, or dimethyl sulfate. Each of those mutation treatments is a method in which a base on a gene is expected to be inserted, deleted, and/or substituted. In each of the mutation treatments, as long as a gene is disrupted, one base may be inserted, deleted, and/or substituted, or a plurality of bases may be inserted, deleted, and/or substituted.

Further, a method involving obtaining a cell of interest from a cell subjected to a mutation treatment is exemplified by a selection method using as an indicator the deletion of an ability to metabolize and decompose myo-inositol or a selection method using as an indicator the level of an activity of an enzyme for inositol catabolism of a cell grown in a medium supplemented with glucose.

In addition, another artificial disruption method for a gene encoding a protein of interest is a method involving inserting, deleting, and/or substituting a base by homologous recombination. The homologous recombination method is a method involving introducing a base sequence partially having the same sequence as a gene of interest subjected to the artificial insertion, deletion, and/or substitution of a base and carrying out mutation by homologous recombination. For example, there is given a method involving introducing a base sequence having inserted thereinto a chloramphenicol-resistant gene, a kanamycin-resistant gene, a tetracycline-resistant gene, an erythromycin-resistant gene, a spectinomycin-resistant gene, an ampicillin-resistant gene, a hygromycin-resistant gene, or the like as a drug-resistant gene and then carrying out selection using the corresponding drug to obtain survival cells. In addition, a cell of interest may be obtained by confirming whether or not the gene was inserted into a desired portion using an instrument such as PCR.

It should be noted that the "artificial disruption of a function of a protein of interest or a gene encoding the protein of interest" refers to, for example, through mutagenesis or homologous recombination, repressing the transcription of the gene, or disrupting a function of a protein encoded by the gene.

The enzymes involved in inositol catabolism and the inositol catabolism are described by way of *Bacillus subtilis* as an example (see FIG. 1). myo-Inositol-2-dehydrogenase is the first enzyme for myo-inositol catabolism encoded by the iolG gene (also described simply as iolG) as one of the genes involved in inositol catabolism. myo-Inositol-2-dehydrogenase converts myo-inositol (MI) to 2-keto-myo-inositol (2KMI) (also referred to as "scyllo-inosose") through an $NAD^+$-dependent reaction. myo-Inositol-2-dehydrogenase also catalyzes a reaction of converting D-chiro-inositol (DCI) to 1-keto-D-chiro-inositol (1KDCI).

Figure 1:
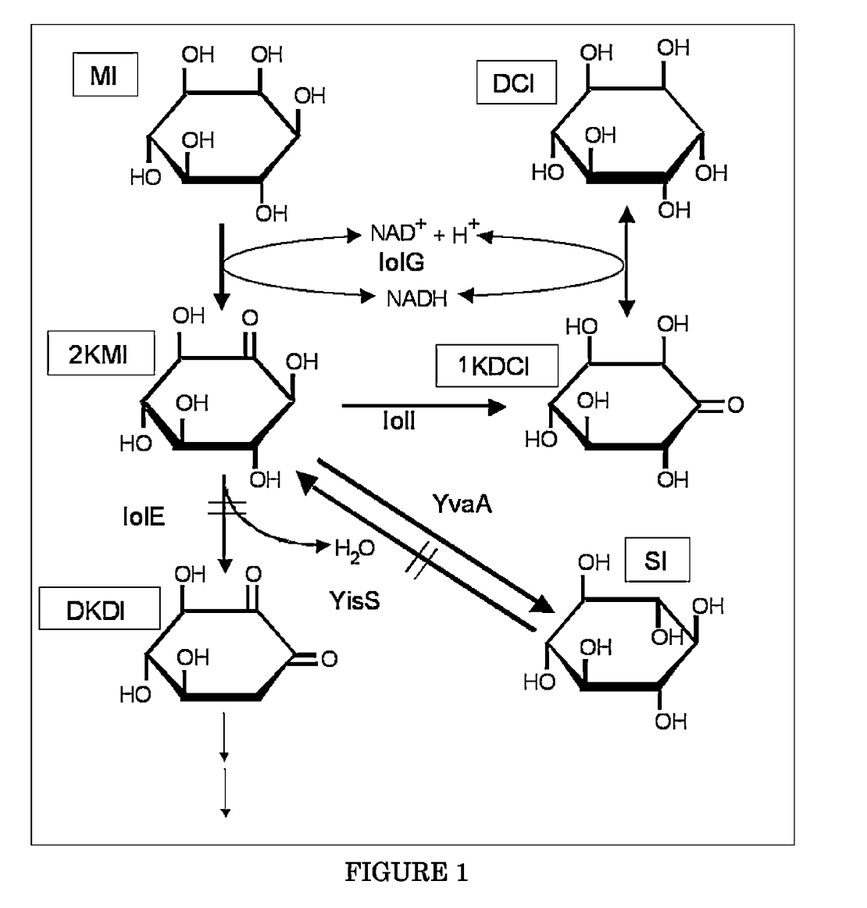
FIG. 1 is a diagram illustrating inositol catabolism in *Bacillus subtilis*.

2-Keto-myo-inositol ketoreductase is an enzyme encoded by the yvaA gene (also described simply as yvaA) (Swiss-Prot: O32223). The presence of a protein having a 2-keto-myo-inositol ketoreductase activity in *Bacillus subtilis* was confirmed in the present invention for the first time. 2-Keto-myo-inositol ketoreductase is an enzyme for converting 2-keto-myo-inositol (2KMI) to scyllo-inositol (SI). Such reaction is dependent on NADPH.

scyllo-Inositol dehydrogenase is an enzyme encoded by the yisS gene (also described simply as yisS) (Swiss-Prot: P40332). The presence of a protein having a scyllo-inositol dehydrogenase activity in *Bacillus subtilis* was confirmed in the present invention for the first time. scyllo-Inositol dehydrogenase converts scyllo-inositol (SI) to 2-keto-myo-inositol (2KMI) and dehydrogenates a hydroxy group at the 2-position of scyllo-inositol. The conversion reaction is an $NAD^+$-dependent reaction.

scyllo-Inosose isomerase is an enzyme encoded by the iolI gene (also described simply as iolI) as one of the genes involved in inositol catabolism and an enzyme for interconverting (isomerizing) 2-keto-myo-inositol (2KMI) and 1-keto-D-chiro-inositol (1KDCI).

Further, 2-keto-myo-inositol dehydratase is encoded by the iolE gene (also described simply as iolE) as one of the genes involved in inositol catabolism and is an enzyme for converting 2-keto-myo-inositol (2KMI) to D-2,3-diketo-4-deoxy-epi-inositol (DKDI) through dehydration.

Another example of the enzymes encoded by the genes involved in inositol catabolism is an enzyme for further metabolizing D-2,3-diketo-4-deoxy-epi-inositol (DKDI). However, when D-2,3-diketo-4-deoxy-epi-inositol (DKDI) is not generated (for example, when no 2-keto-myo-inositol dehydratase activity exists), D-2,3-diketo-4-deoxy-epi-inositol (DKDI) catabolism does not occur.

It is known that almost no expression of the genes involved in inositol catabolism is observed in a culture medium containing myo-inositol but simultaneously containing a sugar such as glucose in *Bacillus subtilis* (Yoshida, K. et al., Nucleic Acids Resarch, vol. 29, p. 683-692 (2001)). Thus, under a general culture condition containing glucose and the like, the activity of each of enzymes for the genes involved in inositol catabolism is very low and conversion reactions of myo-inositol (MI) to scyllo-inositol (SI) and D-chiro-inositol (DCI) hardly proceed.

A gene for transcriptional control protein is known to locate upstream of the genes involved in inositol catabolism. Such transcriptional control protein is a repressor protein encoded by the iolR gene (also described simply as iolR) and is also referred to as negative regulator or negative transcriptional regulator. It is known that an inositol catabolic intermediate 2-deoxy-5-keto-D-glucuronic acid 6-phosphate acts as an inducer on such repressor protein, resulting in the transcriptional derepression of the genes involved in inositol catabolism and the translational induction of enzymes for the genes involved in inositol catabolism (Yoshida, K. et al., Journal of Biological Chemistry, Vol. 283, p. 10415-10424 (2008)). Further, it has been experimentally demonstrated that the disruption of iolR gene also results in the transcriptional derepression of the genes involved in inositol catabolism and the genes involved in inositol catabolism are constitutively expressed (Yoshida, K. et al., Journal of Molecular Biology, Vol. 285, 917-929 (1999)).

For example, in a *Bacillus subtilis* strain (strain YF256) in which a gene encoding a protein having a 2-keto-myo-inositol dehydratase activity (iolE) and a gene encoding a repressor protein for genes involved in inositol catabolism (iolR) were disrupted among the genes involved in inositol catabolism, the conversion efficiency of myo-inositol to D-chiro-inositol was increased. This is because the enzymes for the genes involved in inositol catabolism excluding 2-keto-myo-inositol dehydratase can be biologically synthesized in a transcriptional derepression state, which allows preventing myo-inositol from being undesirably metabolized and decomposed.

A conversion reaction of 2-keto-myo-inositol (2KMI) to 1-keto-D-chiro-inositol (1KDCI) is involved in such conversion of myo-inositol to D-chiro-inositol, and such reaction is catalyzed by scyllo-inosose isomerase. It has been reported that iolI encodes scyllo-inosose isomerase among the genes involved in inositol catabolism of *Bacillus subtilis* (Yoshida, K. et al., Applied and Environmental Microbiology, 72(2), 1310-5 (2006 Feb)).

The inventors of the present invention have newly confirmed that a protein encoded by each of yisS and yvaA in *Bacillus subtilis* is involved in the conversion between scyllo-inositol and 2-keto-myo-inositol, and have produced *Bacillus subtilis* in which not only iolE and iolR but also yisS (gene encoding a protein having a scyllo-inositol dehydrogenase activity) necessary for the decomposition of scyllo-inositol were disrupted (strain TM030). Cells of strain TM030 were cultured in a medium with myo-inositol. As a result, the inventors have found that the strain can produce scyllo-inositol efficiently as compared to strain YF256.

A mutant strain of *Bacillus subtilis* (named strain TM030) obtained by inactivating iolE by drug-induced mutation and disrupting each of iolR and yisS by the insertion of a drug-resistant marker (chloramphenicol-resistant gene, for example, chloramphenicol acetyltransferase) and an integration vector pMUTIN (Vagner, V. et al., Mirocbilogy, Vol. 144, p. 3097-3104 (1998)) through homologous recombination was internationally deposited at the National Institute of Advanced Industrial Science and Technology International Patent Organism Depositary (Central 6, 1-1-1 Higashi, Tsukuba, Ibaraki 305-8566) under an accession number of FERM ABP-11185 (domestic deposit number: FERM P-21700, domestic deposit date: Oct. 8, 2008). The reference Yoshida, K. et al., Microbiology, Vol. 150, p. 571-580 (2004) was modified and used as for a method of disrupting a gene and a specific protocol for selection.

The inventors of the present invention have produced *Bacillus subtilis* in which not only iolE, iolR, and yisS (gene encoding a protein having a scyllo-inositol dehydrogenase activity) but also iolI (gene encoding a protein having a scyllo-inosose isomerase activity) were disrupted (strain TM039). Specifically, in the mutant strain TM030 of *Bacillus subtilis*, iolI was disrupted by the insertion of a spectinomycin-resistant gene through homologous recombination to produce another mutant *Bacillus subtilis* strain (named strain TM039). Cells of strain TM039 were cultured in a medium with myo-inositol. As a result, the inventors have found that scyllo-inositol can be produced with high purity by the strain. It should be noted that the reference Yoshida, K. et al., Microbiology, Vol. 150, p. 571-580 (2004) and Yoshida, K. et al., J. Bacteriol. Vol. 181, p. 6081-6091 (1999) was modified and used as for a method of disrupting a gene and a specific protocol for selection.

The present invention also encompasses a method of manufacturing scyllo-inositol. The method of manufacturing scyllo-inositol includes the step of culturing the cell of the present invention, in which at least a function of a protein having a scyllo-inositol dehydrogenase activity is lost or reduced, in a culture medium containing myo-inositol. In addition, the method of manufacturing scyllo-inositol of the present application preferably includes the steps: removing the cell from a filtrate of the culture obtained in the culturing step; and isolating scyllo-inositol from the filtrate after the removing of the cell.

The medium contains myo-inositol and the composition is not particularly limited as long as the object of the present invention is achieved. The medium has only to be a medium containing a carbon source, a nitrogen source, an organic nutrient source, an inorganic salt, and the like in addition to myo-inositol as a raw material, and any of a synthetic medium and a natural medium may be used. It should be noted that the medium is preferably a broth (liquid medium).

For example, a blend prepared as described below is preferably used for the medium. It is desired to add myo-inositol at 0.1 wt % to 40 wt %, preferably 1 wt % to 30 wt %, more preferably 1 wt % to 10 wt %, to add a carbon source such as malic acid, glycerol, sucrose, maltose, or starch at 0.1 wt % to 20 wt %, more preferably 0.3 wt % to 5 wt %, and to add a nitrogen source such as soytone, casamino acid, peptone, yeast extract, ammonium sulfate, ammonium chloride, ammonium nitrate, or urea at 0.01 wt % to 5.0 wt %, preferably 0.5 wt % to 2.0 wt % with respect to the total weight of the medium.

In addition, as necessary, inorganic salts capable of generating ions such as sodium, potassium, calcium, magnesium, cobalt, manganese, zinc, iron, copper, molybdenum, phosphate, and sulfate ions may be added in a medium. The addition amounts of the inorganic salts may be arbitrarily determined by a person skilled in the art.

The hydrogen ion concentration in a culture medium does not need to be particularly adjusted but may be adjusted to preferably a pH of 5 to 10, more preferably a pH of 6 to 9 before culture.

The culture conditions vary depending on the kind of becteria, and the culture temperature may be set to 12 to 45° C., preferably 15 to 37° C. Further, culture may be performed under an aerobic condition, for example, by shaking a culture medium or blowing air or oxygen gas into a culture medium. The culture has only to be performed until a maximum or requisite amount of scyllo-inositol is accumulated, and the culture period is generally 1 to 7 days, preferably 1 or 2 days.

The culture medium after culturing the cell may contain not only scyllo-inositol but also myo-inositol and D-chiro-inositol. For example, when cells of strain TM030 is cultured, the culture medium may contain scyllo-inositol, myo-inositol, and D-chiro-inositol, and when cells of strain TM039 is cultured, the culture medium does not contain D-chiro-inositol and may contain scyllo-inositol and myo-inositol. A method known per se or a method to be developed in the future may be employed as a method involving fractionating scyllo-inositol from a culture medium. It should be noted that the fractionation of scyllo-inositol may be carried out at a purification degree depending on the purposes, and scyllo-inositol may be fractionated as a mixture of scyllo-inositol and D-chiro-inositol, a mixture of scyllo-inositol and myo-inositol, and the like.

For example, a general method of isolating and purifying a common water-soluble neutral substance is applicable to a method of harvesting scyllo-inositol from a culture medium. That is, almost all of impurities excluding inositols may be removed by removing a bacterial cell from a culture medium and then treating the culture supernatant solution with activated carbon, an ion-exchange resin, or the like. After that, a method such as recrystallization may be employed to isolate a target substance.

Specifically, for example, a culture supernatant solution in which scyllo-inositol has been accumulated is passed through a column filled with a strongly acidic cation-exchange resin such as a Duolite (registered trademark) C-20 (H+-type) for the purpose of removing undesired components, and the passed solution is collected. Then, deionized water is passed through the column for washing, and the washing solution is collected. The resultant passed solution and washing solution are combined with each other. The solution thus obtained is passed through a column filled with a strongly basic anion-exchange resin such as a Duolite (registered trademark) A116 (OH−-type), and the passed solution is collected. Then, deionized water is passed through the column for washing, and the washing solution is collected. The resultant passed solution and washing solution are combined with each other to afford an aqueous solution containing inositols and only few impurities excluding inositols. The aqueous solution is concentrated and the resultant concentrated solution of scyllo-inositol is supplemented with an appropriate amount of ethanol. The mixture is left to stand at room temperature or a lower temperature overnight to deposit pure scyllo-inositol crystals. Further, the pure scyllo-inositol crystals may also be deposited by simply concentrating and filtering the aqueous solution taking advantage of low water solubility of scyllo-inositol. In addition, during carrying out a column operation, a column filled with activated carbon may also be used for the purpose of decolorization.

The pure scyllo-inositol crystals may also be obtained by another purification method such as a method involving adding boric acid and NaCl to a solution containing scyllo-inositol obtained by culture to form a scyllo-inositol-boric acid complex, separating the complex by filtration, then releasing boric acid from the complex with an acid, and adding an organic solvent such as methanol for crystallization (Patent Literature 2).

EXAMPLES

Hereinafter, the present invention is specifically described by way of reference examples and examples in order to gain a further understanding of the present invention. The reference examples describe the processes until the completion of the present invention and the examples specifically describe the contents of the invention. It goes without saying that those examples do not limit the scope of the present invention.

Reference Example 1

Analysis of Culture Medium of Mutant *Bacillus subtilis* Strain YF256

Mutant cells of *Bacillus subtilis* strain (*Bacillus subtilis* strain YF256, deposit number FERM P-20286) were inoculated into a 500 ml Sakaguchi flask containing 30 ml of a broth medium (1 wt % soytone, 0.5 wt % yeast extract, 0.5 wt % NaCl, 1 wt % myo-inositol) and were allowed to grow under an aerobic condition at 37° C. for 17 hours. The culture medium was subjected to centrifugation (10,000 rpm, 15 minutes) to collect a culture supernatant solution.

The culture supernatant solution was analyzed by high performance liquid chromatography under the following conditions.

Column: Wakosil 5NH$_2$ (4.6×250 mm)
Column temperature: 20 ° C. or 40 ° C.
Detector: RI DETECTOR L-2490 (Hitachi)
Injection amount: 10 µl
Solvent: acetonitrile:water=4:1
Flow rate: 2 ml/min
Dissolution time: D-chiro-inositol; 11.6 minutes
myo-Inositol; 17.8 minutes
scyllo-Inositol; 18.2 minutes The results revealed that the peak attributed to scyllo-inositol was detected shortly after the peak to myo-inositol, indicating that Y256 strain is able to produce scyllo-inositol.

Reference Example 2

Search for gene Associated with Scyllo-Inositol Catabolic Function

Paralogou genes exhibiting a high sequence homology to iolG were searched from the genome of *Bacillus subtilis* using a database SSDB (http://ssdb.genome.jp/ssdb-bin/ssdb_paralog?org_gene=bsu:BSU39700). As a result, seven paralogs were selected; namely yfil, yhjJ, yisS, yrbE, yteU, yulF, and yvaA.

A transcriptome analysis was carried out to examine the expression of these genes in the presence of various inositols; scyllo-inositol (SI), myo-inositol (MI), D-chiro-inositol (DCI), and D-pinitol (PI). Each culture operation was as described below. A wild-type *Bacillus subtilis* strain or mutant strain Y256 were cultured with shaking at 37° C. until the middle-logarithmic growth phase using a synthetic medium containing 0.5% casamino acid as a carbon source supplemented with the above-mentioned inositols at 10% (S6 medium; Yoshida, K. et al., Journal of Bacteriology, Vol. 79, p. 4591-4598 (1997)). A DNA array used was the Pan-orama™ Gene Array manufactured by Sigma-Genosys. In Northern blotting, with use of part of yisS structural-gene region amplified by PCR as a template, a DNA probe (380 by corresponding to 415 bp to 794 bp following the translation start site of the yisS structural gene) radiolabeled by a random-primed method involving incorporating $^{32}$P-phosphorous group was used.

Figure 2:
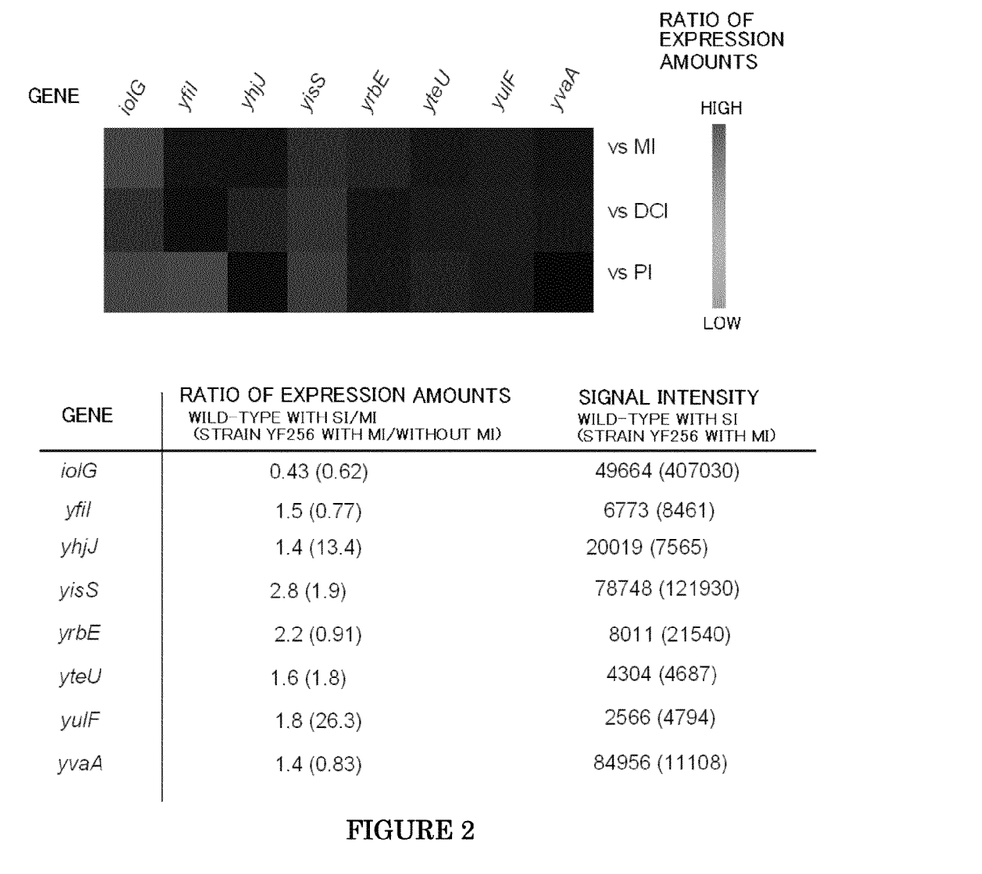
FIG. 2 is a diagram illustrating the results of expression analysis for various genes (Reference Example 2).
Figure 3:
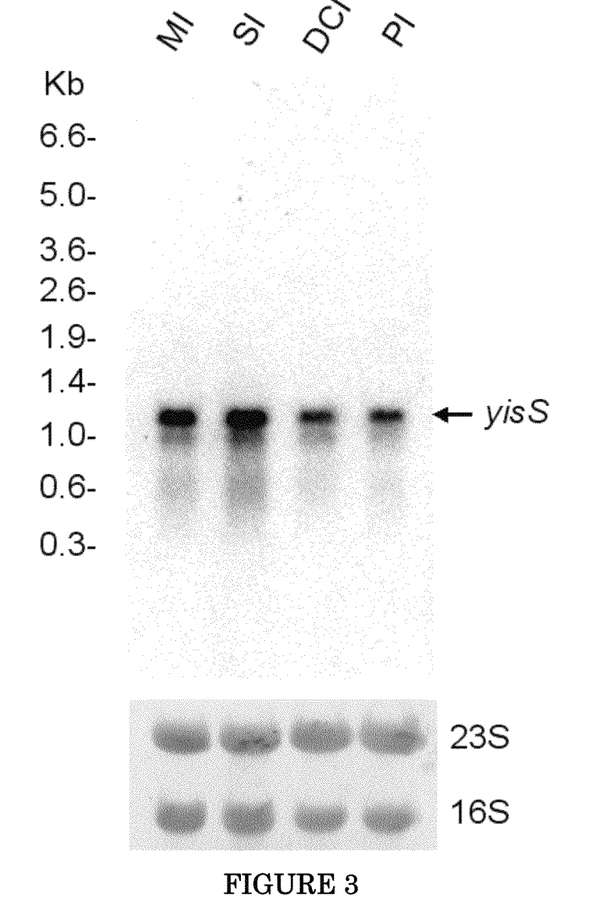
FIG. 3 is a photograph showing the results of confirmation of expression amounts of yisS gene (Reference Example 2).

FIG. 2 and FIG. 3 illustrate the results. The upper part of FIG. 2 is a graphical presentation showing the results of the microarray and the lower part a table for numerical values of the results. FIG. 3 is a photograph showing the results of the Northern blotting.

The results suggested that yisS and yvaA were expressed at high levels as compared to other genes, and in particular, yisS was induced under the growth conditions with scyllo-inositol, which may allow the decomposition and utilization of scyllo-inositol. Accordingly, the results suggested that either or both of yisS and yvaA might encode dehydrogenase whose substrate is scyllo-inositol.

Reference Example 3

Confirmation of Function of yisS Gene

The function of yisS was confirmed by producing a yisS -disrupted strain. The yisS gene was disrupted using a pMUTIN4MCS plasmid. Part of yisS was amplified by PCR using a specific primer pair (designed so that the region corresponding to the chromosomal base numbers of U.S. Pat. Nos. 1,163,917 to 1,164,171 of the *Bacillus subtilis* strain 168 was amplified) and DNA of the wild-type strain 168 of *Bacillus subtilis* serving as a template. The PCR product was digested with an restriction enzyme set of HindIII and BamHI (or BglII) and ligated to the arms of pMUTIN4MCS which had been cleaved with the same enzyme set (Vagner, V. et al., 1998). The recombinant plasmid pMUTIN4MCS thus produced was used to transform the wild type strain 168. Erythromycin resistance was imparted to the transformants by PMUTIN4MCS, which allowed the selection. Such selection gave strain BSF3018, which is included in a bank of mutant strains produced through the *Bacillus subtilis* genome functional analysis project (Kobayashi, K. et al., Proc. Natl. Acad. Sci. USA Vol. 100, p. 4678-4685 (2003)). The bank of mutant strains is maintained at the National Institute of Genetics and can be freely distributed to the public as part of the National BioResource Project (http://www.nbrp.jp/report/reportProject.jsp;jsessionid=6C442727811FEDB94CF60031CCDAF E92.1b1?project=bsub). A tryptophan auxotrophic mutation called trpC2 is included in strain BF3018.

Strain BFS3018 was grown in the presence of glucose (Gluc), in the presence of myo-inositol (MI), and in the presence of scyllo-inositol (SI) and was observed. The wild-type strain and strain YF248 (which cannot metabolize all of inositols because of lacking the expression of all of enzymes involved in inositol catabolism owing to the disruption of promoters for operons involved in inositol catabolism) were used as controls.

Figure 4:
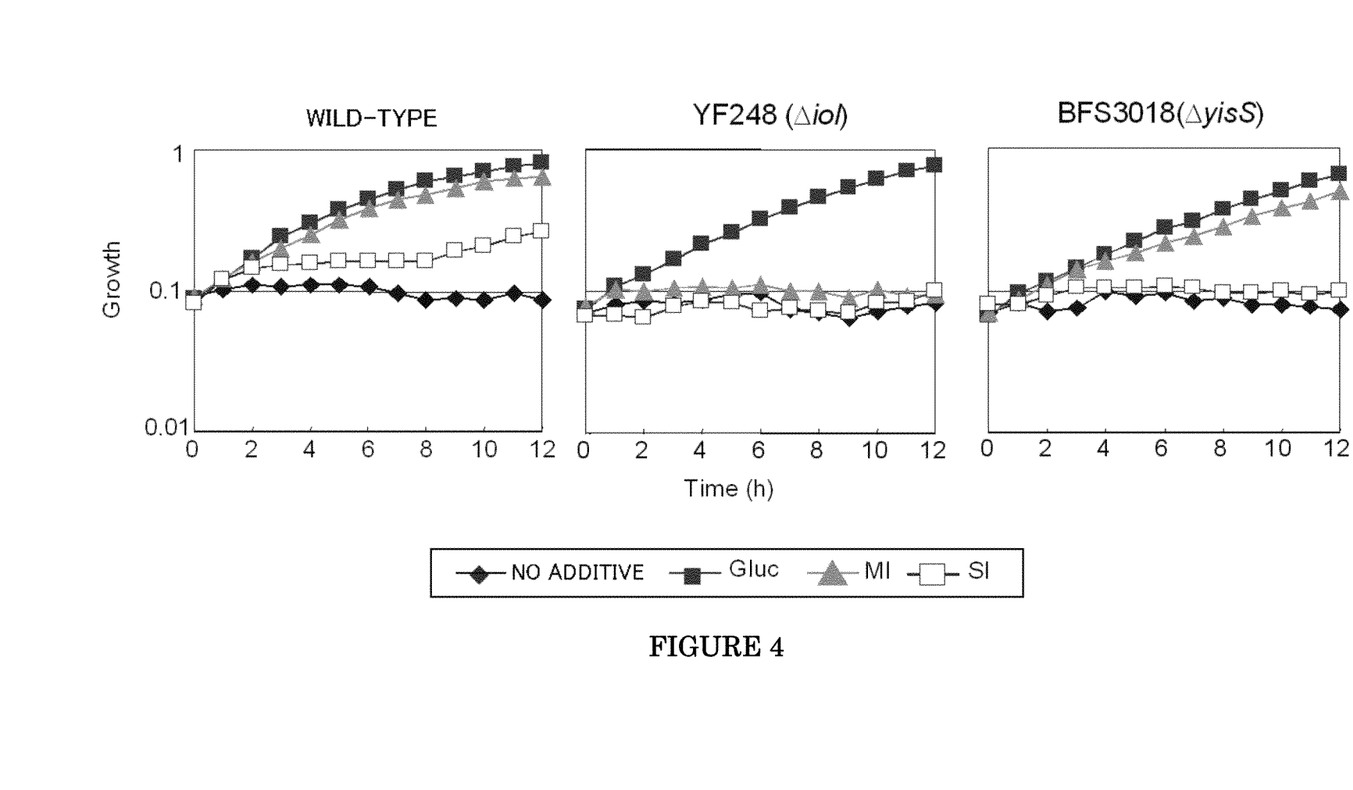
FIG. 4 is a diagram illustrating the results of culture of a yisS gene-disrupted strain (Reference Example 3).
Figure 5:
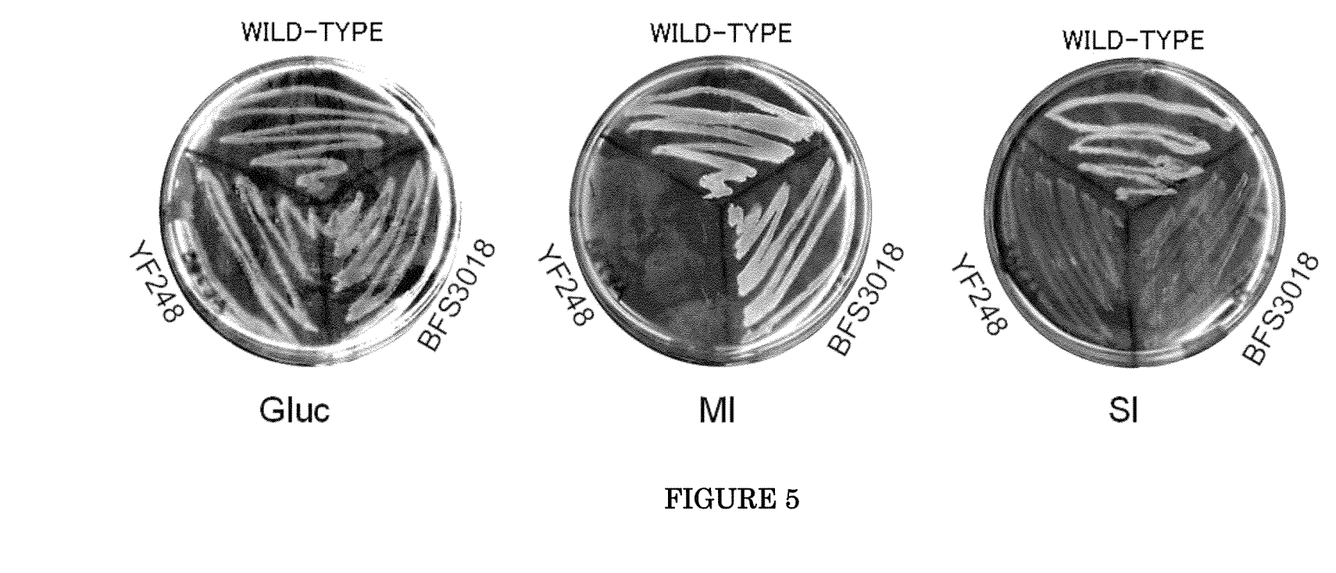
FIG. 5 is a photograph showing the results of culture of a yisS gene-disrupted strain (Reference Example 3).

FIG. 4 and FIG. 5 illustrate the results. FIG. 4 is a graph showing time-dependent changes in cell growth (the longitudinal axis represents an absorbance at a wavelength of 660 nm) and FIG. 5 is a photograph showing cell growth after 30 hours.

In strain BFS3018, cell growth was observed in the presence of glucose and in the presence of myo-inositol, whereas cell growth was not observed in the presence of scyllo-inositol. The results suggested that yisS could encode a protein functioned as an enzyme for metabolizing scyllo-inositol.

Example 1

Production of Scyllo-Inositol-Producing Mutant Strain

Strain YF256 was transformed with DNA of strain BFS3018 to disrupt yisS as follows. Using the competent-cell transformation method, strain YF256 was transformed to be erythromycin-resistant by a homologous recombination so that part of chromosomal DNA of BFS3018 strain was introduced. The resultant transformant was due to possess yisS disrupted by pMUTIN4MCS integration similarly to that in strain BFS3018. Thus, such a transformant was selected to yield strain TM030.

Example 2

Method of Manufacturing Scyllo-Inositol

Mutant cells of strain TM030 was inoculated into a 500 ml Sakaguchi flask containing 30 ml of a broth medium (1 wt % soytone, 0.5 wt % yeast extract, 0.5 wt % NaCl, 1 wt % myo-inositol) and were allowed to grow under an aerobic condition at 37° C. for 17 hours. The culture medium was centrifuged (10,000 rpm, 15 minutes) to collect a culture supernatant solution.

The culture supernatant solution was analyzed by high performance liquid chromatography under the following conditions.

Column: Wakosil 5NH$_2$ (4.6×250 mm)
Column temperature: 20° C.
Detector: RI DETECTER L-2490 (Hitachi)
Injection amount: 10 μl
Solvent: Acetonitrile:water=4:1
Flow rate: 2 ml/min
Dissolution time: D-chiro-inositol; 11.6 minutes
myo-Inositol; 17.8 minutes
scyllo-Inositol; 18.2 minutes The conversion rate of scyllo-inositol was calculated as a percentage of the number of moles of scyllo-inositol in the culture supernatant solution with respect to that of myo-inositol initially contained in the culture medium.

Strain TM030 gave a conversion efficiency of myo-inositol to scyllo-inositol of 16.1% and a conversion efficiency of myo-inositol to D-chiro-inositol of 4.3%.

Strain YF256 gave conversion efficiencies to scyllo inositol and D-chiro-inositol of 6.4% and 8.3%, respectively.

Example 3

Production of Scyllo-Inositol-Producing Mutant Strain 2

Strain TM030 was manipulated additionally to disrupt its iolI. Disruption of iolI was done by the insertion of a spectinomycin-resistant gene through homologous recombination.

In this way, mutant strain TM039 was produced. A specific method was carried out in almost the same manner as described previously in disrupting asnH: Yoshida, K. et al. J. Bacteriol. Vol. 181, p. 6081-6091 (1999). Briefly, 194 by corresponding to 335 by to 528 by following the translation start site of the iolI structural gene was replaced by the spectinomycin-resistant gene.

With use of the chromosome of *Bacillus subtilis* strain 168 as a template, DNA fragments corresponding to the first half portion (including 334 by from the translation start site) and the second half portion (including 529 by and the remaining portion) of Ion were amplified by PCR using a primer pair of iolI1F: TGCGGTTGAACTTGAAGTGG (SEQ ID NO: 5) and iolI2R: TCTTCTGCTCTGTCACAAGC (SEQ ID NO: 6) and a primer pair of iolI5F: CACTTCCATG-CAATGGGTTC (SEQ ID NO: 7) and iolI6R: ATAT-TGATCTTCGCGTGGCC (SEQ ID NO: 8), respectively.

Meanwhile, another DNA fragment of a spectinomycin-resistant gene cassette was amplified by PCR using the chromosome of a strain FU341 (a mutant strain of Bacillus subtilis in which asnH was disrupted by the insertion of the spectinomycin-resistant gene) as a template and a primer pair of iolI3F:

```
                                     (SEQ ID NO: 9)
GCTTGTGACAGAGCAGAAGACAATAACGCTATTGGGAG
and iolI4R:
                                     (SEQ ID NO: 10)
GAACCCATTGCATGGAAGTGCTATATGCTCCTTCTGGC.
```

The above-mentioned three DNA fragments corresponding to the first half portion of Ion, the spectinomycin-resistant gene cassette, and the second half portion of IolI were ligated to one another in the above-mentioned order. The three DNA fragments were combined in an equimolar mixture as the template for PCR amplification using primers of iolI1F: TGCGGTTGAACTTGAAGTGG (SEQ ID NO: 5) and iolI6R: ATATTGATCTTCGCGTGGCC (SEQ ID NO: 8). The resultant PCR-ligated DNA was used in an appropriate amount to transform strain TM030 so that spectinomycin resistance was imparted, to thereby afford strain TM039.

Example 4

Method of Manufacturing Scyllo-Inositol 2

Mutant strains TM039, TM030, or YF256 were cultured by the same technique as that in Example 2. After that, the culture medium was centrifuged (10,000 rpm, 15 minutes) to collect a culture supernatant solution.

The culture supernatant solution was analyzed by the same technique as that in Example 2 using high performance liquid chromatography.

The conversion rate of scyllo-inositol was calculated as a percentage of the number of moles of scyllo-inositol in the culture supernatant solution with respect to that of myo-inositol contained initially in the culture medium.

Figure 6:
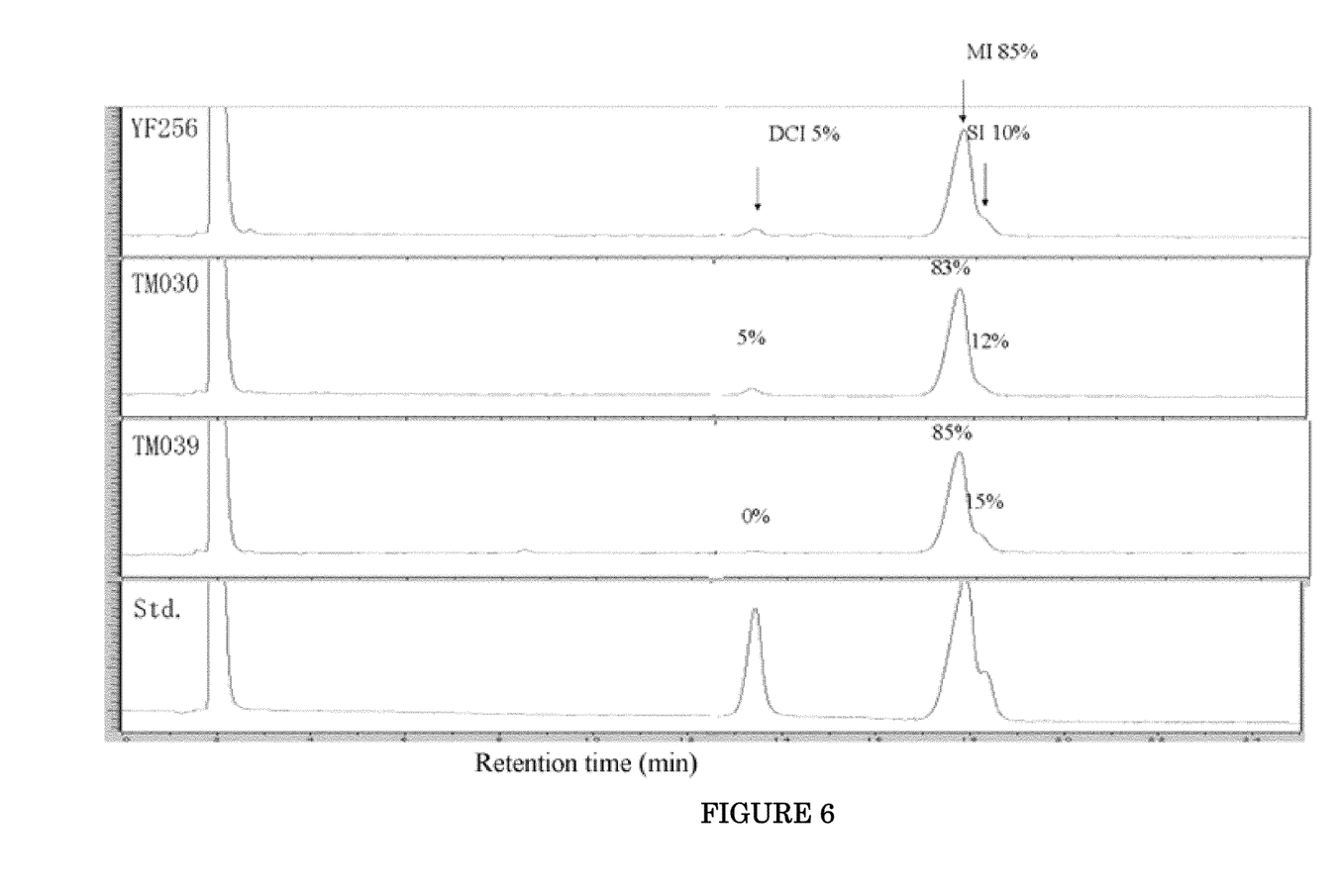
FIG. 6 is a chart showing the results of analysis of a culture medium in which a strain TM039 was cultured (Example 4).

FIG. 6 illustrates the results.

Strain TM030 gave a conversion efficiency of myo-inositol to scyllo-inositol of 12% and a conversion efficiency of myo-inositol to D-chiro-inositol of 5%.

Strain TM039 gave a conversion efficiency of myo-inositol to scyllo-inositol of 15% and a conversion efficiency of myo-inositol to D-chiro-inositol of 0%.

Meanwhile, strain YF256 gave conversion efficiencies to scyllo inositol and D-chiro-inositol of 10% and 5%, respectively.

INDUSTRIAL APPLICABILITY

The method of manufacturing scyllo-inositol using the cell of the present invention is useful because the method allows simply manufacturing scyllo-inositol, which can be extracted only in a trace amount from a naturally occurring raw material, from myo-inositol, which is supplied at low cost, with high purity.

A variety of studies have been hitherto conducted on a therapeutic effect of scyllo-inositol on Alzheimer's disease. For example, it has been reported that, in neurons, scyllo-inositol suppresses the aggregation of fβ-amyloid as a possible cause of Alzheimer's disease, and further, scyllo-inositol had no toxicity on neurons (McLaurin J. et al., J Biol Chem. Vol. 275, p. 18495-18502 (2000); Sun Y., et al., Bioorg Med Chem. Vol. 16, p. 7177-7184 (2008)). Further, it has been found out that, in an Alzheimer's disease mouse model, the oral intake of scyllo-inositol suppresses the aggregation of fβ-amyloid in the brain, and it has been demonstrated that scyllo-inositol alleviates cognitive symptoms in Alzheimer's disease and inhibits reduced life expectancy (Fenili D. et al., J Mol Med. Vol. 85, 603-611 (2007); Townsend M. et al., Ann Neurol. Vol. 60, p. 668-676 (2006)).

It is conceivable that scyllo-inositol has high safety as compared to other compounds, and is not involved in an immune reaction and thus does not cause allergy. In addition, scyllo-inositol can easily pass through the blood-brain barrier into the brain, and hence can be administered to a living body through oral administration. scyllo-Inositol is therefore a substance with extremely high practicability in the prevention and treatment of Alzheimer's disease. The cell of the present invention allows such scyllo-inositol to be efficiently produced with high purity.

The invention claimed is:

1. A method for producing scyllo-inositol, said method comprising culturing a scyllo-inositol-producing cell in a culture medium comprising myo-inositol under conditions sufficient to produce scyllo-inositol from myo-inositol, wherein said scyllo-inositol-producing cell has lost or has reduced scyllo-inositol dehydrogenase activity due to artificial disruption or mutation of a gene encoding a protein having scyllo-inositol dehydrogenase activity, wherein said protein having scyllo-inositol dehydrogenase activity is selected from the protein consisting of:
   (a) a protein comprising an amino acid sequence set forth in SEQ ID NO: 2;
   (b) a protein comprising an amino acid sequence having deletions, substitutions, insertions, and/or additions of one to 20 amino acids in the amino acid sequence set forth in SEQ ID NO: 2; and
   (c) a protein comprising an amino acid sequence having 95% or more homology to the amino acid sequence set forth in SEQ ID NO: 2.

2. The method for producing scyllo-inositol according to claim 1 further comprising the steps of:
   removing said scyllo-inositol-producing cell from said culture medium to produce a filtrate; and
   isolating scyllo-inositol from said filtrate.

3. The method of claim 1, wherein said scyllo-inositol-producing cell has lost or has reduced scyllo-inositol dehydrogenase activity due to artificial disruption of a gene encoding a protein having scyllo-inositol dehydrogenase activity, wherein said protein having scyllo-inositol dehydrogenase activity is selected from the protein encoded by an oligonucleotide consisting of:
   (a) an oligonucleotide comprising a base sequence set forth in SEQ ID NO: 1;
   (b) an oligonucleotide comprising a base sequence having substitutions, deletions, insertions, and/or additions of one to 20 nucleotides in the base sequence set forth in SEQ ID NO: 1; and
   (c) an oligonucleotide capable of being hybridized with the oligonucleotide comprising the base sequence set forth in SEQ ID NO: 1, at 65° C. in the presence of 0.7 to 1.0 M sodium chloride.

4. The method of claim 1, wherein said scyllo-inositol-producing cell has a functioning 2-keto-myo-inositol ketoreductase activity, wherein 2-keto-myo-inositol ketoreductase activity of said scyllo-inositol-producing cell is due to a presence of a protein selected from the group consisting of:
   (a) a protein comprising an amino acid sequence set forth in SEQ ID NO: 4;
   (b) a protein comprising an amino acid sequence having deletions, substitutions, insertions, and/or additions of one to 20 amino acids in the amino acid sequence set forth in SEQ ID NO: 4; and
   (c) a protein comprising an amino acid sequence having 95% or more homology to the amino acid sequence set forth in SEQ ID NO: 4.

5. The method of claim 1, wherein said scyllo-inositol-producing cell has a functioning 2-keto-myo-inositol ketoreductase activity, wherein 2-keto-myo-inositol ketoreductase activity of said scyllo-inositol-producing cell is due to a presence of a protein encoded by an oligonucleotide selected from the group consisting of:
   (a) an oligonucleotide comprising a base sequence set forth in SEQ ID NO: 3;
   (b) an oligonucleotide comprising a base sequence having substitutions, deletions, insertions, and/or additions of one to 20 nucleotides in the base sequence set forth in SEQ ID NO: 3; and
   (c) an oligonucleotide capable of being hybridized with the oligonucleotide comprising the base sequence set forth in SEQ ID NO: 3 at 65° C. in the presence of 0.7 to 1.0 M sodium chloride.

6. A method for producing scyllo-inositol, said method comprising culturing a scyllo-inositol-producing cell in a culture medium comprising myo-inositol under conditions sufficient to produce scyllo-inositol from myo-inositol, wherein said scyllo-inositol-producing cell has lost or has reduced scyllo-inositol dehydrogenase activity due to artificial disruption of a gene encoding a protein having scyllo-inositol dehydrogenase activity, wherein said protein having scyllo-inositol dehydrogenase activity is selected from the protein encoded by an oligonucleotide consisting of:
- (a) an oligonucleotide comprising a base sequence set forth in SEQ ID NO: 1;
- (b) an oligonucleotide comprising a base sequence having substitutions, deletions, insertions, and/or additions of one to 20 nucleotides in the base sequence set forth in SEQ ID NO: 1; and
- (c) an oligonucleotide capable of being hybridized with the oligonucleotide comprising the base sequence set forth in SEQ ID NO: 1, at 65° C. in the presence of 0.7 to 1.0 M sodium chloride.

7. The method for producing scyllo-inositol according to claim 6 further comprising the steps of:
removing said scyllo-inositol-producing cell from said culture medium to produce a filtrate; and
isolating scyllo-inositol from said filtrate.

8. The method of claim 6, wherein said scyllo-inositol-producing cell has functioning 2-keto-myo-inositol ketoreductase activity, wherein 2-keto-myo-inositol ketoreductase activity of said scyllo-inositol-producing cell is due to a presence of a protein selected from the group consisting of:
- (a) a protein comprising an amino acid sequence set forth in SEQ ID NO: 4;
- (b) a protein comprising an amino acid sequence having deletions, substitutions, insertions, and/or additions of one to 20 amino acids in the amino acid sequence set forth in SEQ ID NO: 4; and
- (c) a protein comprising an amino acid sequence having 95% or more homology to the amino acid sequence set forth in SEQ ID NO: 4.

9. The method of claim 6, wherein said scyllo-inositol-producing cell has functioning 2-keto-myo-inositol ketoreductase activity, wherein 2-keto-myo-inositol ketoreductase activity of said scyllo-inositol-producing cell is due to a presence of a protein encoded by an oligonucleotide selected from the group consisting of:
- (a) an oligonucleotide comprising a base sequence set forth in SEQ ID NO: 3;
- (b) an oligonucleotide comprising a base sequence having substitutions, deletions, insertions, and/or additions of one to 20 or more nucleotides in the base sequence set forth in SEQ ID NO: 3; and
- (c) an oligonucleotide capable of being hybridized with the oligonucleotide comprising the base sequence set forth in SEQ ID NO: 3 at 65° C. in the presence of 0.7 to 1.0 M sodium chloride.

* * * * *

SEQUENCE LISTING

```
<160> NUMBER OF SEQ ID NOS: 10

<210> SEQ ID NO 1
<211> LENGTH: 1029
<212> TYPE: DNA
<213> ORGANISM: Bacillus subtilis

<400> SEQUENCE: 1
gtggaacatc aagtaagatg tgcagtattg ggattaggaa ggctcggtta ttatcatgcg      60
aaaaatctcg tcaccagtgt gccggggca aagctggttt gtgtcggtga tccgttaaaa     120
gggagagcgg agcaggttgc cagagaactc ggtatcgaaa aatggtcaga ggacccgtat    180
gaagtgttag aagatcccgg cattgatgct gtcattatcg taacgccgac aagcacacat    240
ggtgatatga tcatcaaagc agccgagaac ggcaaacaga tctttgttga aaaaccgctg    300
acattaagcc ttgaggaatc aaaagcagct tctgaaaaag ttaaggagac aggtgtcatc    360
tgccaagtcg gctttatgag acggttcgat cccgcatacg cagatgccaa acggcggatc    420
gacgctggag aaatcggcaa acctatctat tataaaggct ttacgcgcga ccaaggcgcg    480
cctcccgcag aatttatcaa acacagcggt ggaatttta tcgactgttc catccatgac    540
tatgatattg cccgttattt gctagggggcg gaaatcactt ctgtttcagg acacggcagg    600
attctgaaca atccgtttat ggagcagtat ggcgatgtgg atcaggcgct gacgtatatt    660
gaatttgact cgggcgcagc gggggacgtc gaggcaagca gaacctctcc atacggacat    720
gacatccggg cggaggtgat cgggacagag ggcagtattt tcatagggac attgagacat    780
caacatgtga ccatcctatc ggctaaaggg agcagttttg atatcattcc agactttcaa    840
actcgttttc atgaagccta ctgcttggag cttcagcatt tcgccgagtg tgtccggaat    900
ggaaaaacac cgattgtgac tgatattgat gcgacgatca atttagaagt gggtatcgcc    960
gcaaccaatt cctttcgaaa cggcatgccg gtacagctag atgtgaagcg cgcttataca   1020
``` ggtatgtaa                                                          1029

<210> SEQ ID NO 2
<211> LENGTH: 342
<212> TYPE: PRT
<213> ORGANISM: Bacillus subtilis

<400> SEQUENCE: 2

Met Glu His Gln Val Arg Cys Ala Val Leu Gly Leu Gly Arg Leu Gly
1               5                   10                  15

Tyr Tyr His Ala Lys Asn Leu Val Thr Ser Val Pro Gly Ala Lys Leu
            20                  25                  30

Val Cys Val Gly Asp Pro Leu Lys Gly Arg Ala Glu Gln Val Ala Arg
        35                  40                  45

Glu Leu Gly Ile Glu Lys Trp Ser Glu Asp Pro Tyr Glu Val Leu Glu
    50                  55                  60

Asp Pro Gly Ile Asp Ala Val Ile Ile Val Thr Pro Thr Ser Thr His
65                  70                  75                  80

Gly Asp Met Ile Ile Lys Ala Ala Glu Asn Gly Lys Gln Ile Phe Val
                85                  90                  95

Glu Lys Pro Leu Thr Leu Ser Leu Glu Glu Ser Lys Ala Ala Ser Glu
            100                 105                 110

Lys Val Lys Glu Thr Gly Val Ile Cys Gln Val Gly Phe Met Arg Arg
        115                 120                 125

Phe Asp Pro Ala Tyr Ala Asp Ala Lys Arg Arg Ile Asp Ala Gly Glu
    130                 135                 140

Ile Gly Lys Pro Ile Tyr Tyr Lys Gly Phe Thr Arg Asp Gln Gly Ala
145                 150                 155                 160

Pro Pro Ala Glu Phe Ile Lys His Ser Gly Gly Ile Phe Ile Asp Cys
                165                 170                 175

Ser Ile His Asp Tyr Asp Ile Ala Arg Tyr Leu Leu Gly Ala Glu Ile
            180                 185                 190

Thr Ser Val Ser Gly His Gly Arg Ile Leu Asn Asn Pro Phe Met Glu
        195                 200                 205

Gln Tyr Gly Asp Val Asp Gln Ala Leu Thr Tyr Ile Glu Phe Asp Ser
    210                 215                 220

Gly Ala Ala Gly Asp Val Glu Ala Ser Arg Thr Ser Pro Tyr Gly His
225                 230                 235                 240

Asp Ile Arg Ala Glu Val Ile Gly Thr Glu Gly Ser Ile Phe Ile Gly
                245                 250                 255

Thr Leu Arg His Gln His Val Thr Ile Leu Ser Ala Lys Gly Ser Ser
            260                 265                 270

Phe Asp Ile Ile Pro Asp Phe Gln Thr Arg Phe His Glu Ala Tyr Cys
        275                 280                 285

Leu Glu Leu Gln His Phe Ala Glu Cys Val Arg Asn Gly Lys Thr Pro
    290                 295                 300

Ile Val Thr Asp Ile Asp Ala Thr Ile Asn Leu Glu Val Gly Ile Ala
305                 310                 315                 320

Ala Thr Asn Ser Phe Arg Asn Gly Met Pro Val Gln Leu Asp Val Lys
                325                 330                 335

Arg Ala Tyr Thr Gly Met
            340

<210> SEQ ID NO 3
<211> LENGTH: 1077

```
<212> TYPE: DNA
<213> ORGANISM: Bacillus subtilis

<400> SEQUENCE: 3
ttgataacgc ttttaaaggg gagaagaaaa gtggatacga tcaaggttgg aatattagga      60
tacggattgt ccggttctgt ttttcacggg ccgctgctgg atgttctgga tgaatatcaa     120
atcagcaaaa tcatgacatc acggacagaa gaagtgaaac gggattttcc agatgctgag     180
gttgtacatg agcttgaaga atcacaaat gaccctgcca ttgagcttgt cattgtcacc      240
accccgagcg gccttcatta cgagcatact atggcatgca tacaggccgg aaaacatgtt     300
gtgatggaaa aaccaatgac agcaacggcc gaagaggggg aaacattaaa aagggctgcc     360
gatgaaaaag gcgtattatt aagcgtatat cataaccgac gctgggataa cgatttttta     420
acgattaaaa agctgatctc tgagggatcc cttgaagata tcaatacata tcaagtttcc     480
tataaccgct acagacctga agttcaagcg cggtggcggg aaaaagaagg cactgccact     540
ggtacgctgt atgatctcgg ctcccacatc atagaccaaa ccctgcattt gtttgggatg     600
cctaaagccg tgactgcaaa cgtgatggcc cagcgggaaa atgccgaaac ggttgactat     660
tttcatttaa ccctggatta tggcaagctt caagccattc tatacggagg atcaatcgtt     720
ccggcaaacg gacctcgtta tcaaatccat ggaaaagatt ctagctttat caaatatgga     780
attgacggac aggaagacgc actcagagcg ggaagaaaac cagaggatga cagctggggt     840
gcggatgttc cggagtttta cggaaagctt acaaccattc gtggctccga caaaaaaaca     900
gaaacgattc catcagtaaa tggctcctac cttacttatt accgtaaaat agcggaaagc     960
atacgagaag gtgctgcgct gccagtcact gctgaggaag gtattaatgt catccgcatc    1020
attgaagccg cgatggaaag cagtaaagag aaacgaacca ttatgctgga gcactaa      1077

<210> SEQ ID NO 4
<211> LENGTH: 358
<212> TYPE: PRT
<213> ORGANISM: Bacillus subtilis

<400> SEQUENCE: 4

Met Ile Thr Leu Leu Lys Gly Arg Arg Lys Val Asp Thr Ile Lys Val
1               5                   10                  15

Gly Ile Leu Gly Tyr Gly Leu Ser Gly Ser Val Phe His Gly Pro Leu
            20                  25                  30

Leu Asp Val Leu Asp Glu Tyr Gln Ile Ser Lys Ile Met Thr Ser Arg
        35                  40                  45

Thr Glu Glu Val Lys Arg Asp Phe Pro Asp Ala Val Val His Glu
    50                  55                  60

Leu Glu Glu Ile Thr Asn Asp Pro Ala Ile Glu Leu Val Ile Val Thr
65                  70                  75                  80

Thr Pro Ser Gly Leu His Tyr Glu His Thr Met Ala Cys Ile Gln Ala
                85                  90                  95

Gly Lys His Val Val Met Glu Lys Pro Met Thr Ala Thr Ala Glu Glu
            100                 105                 110

Gly Glu Thr Leu Lys Arg Ala Ala Asp Glu Lys Gly Val Leu Leu Ser
        115                 120                 125

Val Tyr His Asn Arg Arg Trp Asp Asn Asp Phe Leu Thr Ile Lys Lys
    130                 135                 140

Leu Ile Ser Glu Gly Ser Leu Glu Asp Ile Asn Thr Tyr Gln Val Ser
145                 150                 155                 160
```

```
Tyr Asn Arg Tyr Arg Pro Glu Val Gln Ala Arg Trp Arg Glu Lys Glu
                165                 170                 175
Gly Thr Ala Thr Gly Thr Leu Tyr Asp Leu Gly Ser His Ile Ile Asp
            180                 185                 190
Gln Thr Leu His Leu Phe Gly Met Pro Lys Ala Val Thr Ala Asn Val
        195                 200                 205
Met Ala Gln Arg Glu Asn Ala Glu Thr Val Asp Tyr Phe His Leu Thr
    210                 215                 220
Leu Asp Tyr Gly Lys Leu Gln Ala Ile Leu Tyr Gly Gly Ser Ile Val
225                 230                 235                 240
Pro Ala Asn Gly Pro Arg Tyr Gln Ile His Gly Lys Asp Ser Ser Phe
                245                 250                 255
Ile Lys Tyr Gly Ile Asp Gly Gln Glu Asp Ala Leu Arg Ala Gly Arg
            260                 265                 270
Lys Pro Glu Asp Asp Ser Trp Gly Ala Asp Val Pro Glu Phe Tyr Gly
        275                 280                 285
Lys Leu Thr Thr Ile Arg Gly Ser Asp Lys Lys Thr Glu Thr Ile Pro
    290                 295                 300
Ser Val Asn Gly Ser Tyr Leu Thr Tyr Tyr Arg Lys Ile Ala Glu Ser
305                 310                 315                 320
Ile Arg Glu Gly Ala Ala Leu Pro Val Thr Ala Glu Glu Gly Ile Asn
                325                 330                 335
Val Ile Arg Ile Ile Glu Ala Ala Met Glu Ser Ser Lys Glu Lys Arg
            340                 345                 350
Thr Ile Met Leu Glu His
        355

<210> SEQ ID NO 5
<211> LENGTH: 20
<212> TYPE: DNA
<213> ORGANISM: Artificial Sequence
<220> FEATURE:
<223> OTHER INFORMATION: Primer used for PCR amplification

<400> SEQUENCE: 5
tgcggttgaa cttgaagtgg                                              20

<210> SEQ ID NO 6
<211> LENGTH: 20
<212> TYPE: DNA
<213> ORGANISM: Artificial Sequence
<220> FEATURE:
<223> OTHER INFORMATION: Primer used for PCR amplification

<400> SEQUENCE: 6
tcttctgctc tgtcacaagc                                              20

<210> SEQ ID NO 7
<211> LENGTH: 20
<212> TYPE: DNA
<213> ORGANISM: Artificial Sequence
<220> FEATURE:
<223> OTHER INFORMATION: Primer used for PCR amplification

<400> SEQUENCE: 7
cacttccatg caatgggttc                                              20

<210> SEQ ID NO 8
<211> LENGTH: 20
<212> TYPE: DNA
```

```
<213> ORGANISM: Artificial Sequence
<220> FEATURE:
<223> OTHER INFORMATION: Primer used for PCR amplification

<400> SEQUENCE: 8
atattgatct tcgcgtggcc                                               20

<210> SEQ ID NO 9
<211> LENGTH: 38
<212> TYPE: DNA
<213> ORGANISM: Artificial Sequence
<220> FEATURE:
<223> OTHER INFORMATION: Primer used for PCR amplification

<400> SEQUENCE: 9
gcttgtgaca gagcagaaga caataacgct attgggag                            38

<210> SEQ ID NO 10
<211> LENGTH: 38
<212> TYPE: DNA
<213> ORGANISM: Artificial Sequence
<220> FEATURE:
<223> OTHER INFORMATION: Primer used for PCR amplification

<400> SEQUENCE: 10
gaacccattg catggaagtg ctatatgctc cttctggc                            38
```